United States Patent [19]

Boaz

[11] Patent Number: 4,921,798
[45] Date of Patent: May 1, 1990

[54] SYNTHESIS OF (ARYL OR ARYLALKYL)-3-HYDROXY PROPIONIC ACIDS AND ARYL ALKANEDIOLS HAVING HIGH OPTICAL PURITY

[75] Inventor: Neil W. Boaz, Waterloo, N.Y.

[73] Assignee: Eastman Kodak Company, Rochester, N.Y.

[21] Appl. No.: 412,260

[22] Filed: Sep. 25, 1989

[51] Int. Cl.$^5$ .................. C12P 7/42; C12R 1/39; C07P 41/00
[52] U.S. Cl. .................. 435/146; 435/156; 435/197; 435/280; 435/876
[58] Field of Search .............. 435/146, 156, 280, 197, 435/876, 253.3, 136

[56] References Cited

U.S. PATENT DOCUMENTS

| | | | |
|---|---|---|---|
| 4,204,044 | 5/1980 | Suhara et al. | 435/876 |
| 4,629,701 | 12/1986 | Sakimae et al. | 435/280 |
| 4,668,628 | 5/1987 | Dahod et al. | 435/280 |
| 4,734,367 | 3/1988 | Levenberger et al. | 435/146 |
| 4,745,066 | 5/1988 | Hamaguchi et al. | 435/280 |

FOREIGN PATENT DOCUMENTS

| | | | |
|---|---|---|---|
| 1088894 | 5/1986 | Japan | 435/146 |
| 2179651 | 3/1987 | United Kingdom | 435/146 |

OTHER PUBLICATIONS

Laumen, K. E., Ph.D. Thesis, University of Wuppertal, Federal Republic of Germany (1987).
Laumen et al., J. Chem. Soc. Chem. Commun., 1988, pp. 598–600.
Laumen et al., J. Chem. Soc. Chem. Commun., 1988, pp. 1459–1461.
Xie et al., J. Chem. Soc. Chem. Commun., 1988, pp. 966–967.
Wang et al., Tetrahedron Letters, vol. 30, 1989, pp. 1917–1920.
Manzocchi et al., J. Chem. Soc. Perkin Trans. I, 1987, pp. 2753–2757.
Deol et al., Aust. J. Chem., 1976, pp. 2459–2467.
Mukayama et al., Chemistry Letters, pp. 813–816 (1985).
Soai et al., J. Chem. Soc. Chem. Commun., 1985, pp. 138–139.

*Primary Examiner*—Herbert J. Lilling
*Attorney, Agent, or Firm*—Robert A. Linn

[57] ABSTRACT

R- and S-1-Phenyl-1,3-propanediol, each of high optical purity, were prepared by a chemoenzymatic sequence starting with ethyl benzoylacetate. The first step was a catalytic hydrogenation of the $\beta$-ketoester conducted at room temperature. The enzymatic hydrolysis of the resulting hydroxyester proceeded in a facile manner using a commercial preparation of the lipase from *Pseudomonas fluorescens*. The enzymatic hydrolysis proceeded at a moderate rate (350 mg lipase/0.10 mol of racemic ester required a 20-hour reaction time with an enantiomeric rate ratio (E value) of 36). The hydrolysis was run to 45–50% conversion to afford isolated S-3-phenyl-3-hydroxypropionic acid of 85–90% ee after separation from the residual ester (aqueous base extraction). The optical purity of the hydroxy acid was determined by conversion to the methyl ester ($CH_3I$, $KHCO_3$, acetone), and derivatization with S-MTPA-Cl, and $^1H$ NMR analysis. A single recrystallization of the isolated acid afforded optically pure (>98% ee) S-3-phenyl-3-hydroxypropionic acid in an overall 36% yield from the racemic ester. The acid was reduced with borane in THF to afford optically purs S-diol in 97% yield after crystallization. The overall sequence proceeded in 34% total yield from racemic ester with an additional 45–55% recovered as the antipodal ester. This antipodal ester is obtained in 85–95% ee, and the corresponding hydroxy-acid was readily obtained (NaOH), $CH_3OH/H_2O$) and recrystallized to optical purity. Reduction then afforded R-1-phenyl-1,3-propanediol in 30% to overall yield from racemic ester.

7 Claims, No Drawings

SYNTHESIS OF (ARYL OR ARYLALKYL)-3-HYDROXY PROPIONIC ACIDS AND ARYL ALKANEDIOLS HAVING HIGH OPTICAL PURITY

FIELD OF THE INVENTION

This invention relates to the preparation of organic compounds in high optical purity. In a preferred embodiment it relates to the preparation of optically pure, or substantially optically pure 1-phenyl-1,3-propanediols. The process of the invention comprises use of a biocatalytic synthesis rather than one of the classical resolution methods known in the art. More specifically, the process comprises use of a biological material such as an enzyme to hydrolyze one of the optical isomers in a racemic mixture. Both the product of the enzymatic reaction and the unreacted enantiomer are useful as chemical intermediates for the preparation of other compounds having high optical purity.

BACKGROUND OF THE INVENTION

Classically, the resolution of a racemic mixture into enantiomers involves conversion of the racemate into a mixture of diastereomers. The conversion requires use of an optically active reagent. Diastereomers have more than one chiral center and are not mirror images. Thus, they have different achiral properties such as solubility, enabling them to be separated.

The majority of resolutions that have been carried out involve the reaction of organic bases with organic acids to yield salts. For example, when a practitioner wishes to resolve a racemic mixture of an organic acid, he or she reacts the mixture with an optically active base, such as quinine or the like, to prepare the corresponding mixture of salts. The salts in the mixture will have different properties, including solubility. Therefore, they can be separated by fractional crystallization. After the separation has taken place, optically active acid can be recovered from each salt by reaction with strong mineral acid, which displaces the weaker organic acid. If the salt had been purified by repeated recrystallizations to remove traces of the other diastereomer, the acid will be recovered in optically pure form.

Resolution of organic bases is conducted by a reversal of the process. In these instances, the reaction of an optically active acid with the racemic base is followed by repeated fractional crystallizations to separate the diastereomeric salts obtained. Reaction of a strong base with the purified salt displaces the weaker organic base employed in the salt formation.

The resolution of alcohols poses a difficult problem. Alcohols are not strong acids or bases. Hence they cannot be resolved directly by salt formation. To overcome this difficulty, the alcohols are chemically attached to an acid which can form a salt. After the acid is no longer needed, it is removed. Such a resolution process is difficult, expensive, and tedious. Hence, there is a need for improved methods for the resolution of racemic mixtures of alcohols. This invention satisfies that need.

Chemoenzymatic synthesis is a preparative strategy which uses chemical and biological steps in a reaction sequence. The biocatalytic reactions convert one organic compound to another by the use of enzymes, either isolated or as part of a biological system. Biocatalysts are especially useful for the introduction of chiral specificity into a reaction series.

The major drawback of biocatalytic systems is an unpredictable substrate specificity due to the lack of knowledge concerning the steric requirements of the enzyme's active site. Further complications can arise from enzyme inhibition caused by either the substrate or product.

With regard to the instant invention, Applicant was faced with the task of preparing optically pure diols. These diols are not strong acid or bases; hence, as pointed out above, the resolution of a racemic mixture of such materials presents a difficult task. Furthermore, the molecules of interest have a hydrophilic group substituted on a carbon alpha to a phenyl group. Up to the present invention, it was not known whether lipase from *Pseudomonas fluorescens* (or a similar enzyme) would accept and convert an ester precursor of such diol in a hydrolysis reaction. Applicant discovered that the enzyme would operate on such a substrate; this discovery was wholly unpredictable from the prior art.

Furthermore, Applicant discovered that the product of the reaction did not poison the enzyme to an extent which would prevent its use in a viable resolution process. In addition, Applicant also discovered a set of reaction conditions which permitted preparation of the desired diols in high optical purity. Moreover, Applicant discovered an elegant chemical synthesis for the preparation of a racemic ester used in the reaction step in which the enzyme is employed. This synthesis step affords a nearly quantitative yield of the substrate in a form which does not require purification before subjecting it to the action of the enzyme. In view of these discoveries, it is believed that Applicant's chemoenzymatic synthesis is a significant advance in the art.

RELATED ART

Active site steric models are known for several hydrolase enzymes. Among these is the lipase from *Pseudomonas fluorescens;* Laumen, K. E., Ph. D. Thesis, University of Wuppertal, Federal Republic of Germany, 1987. The enzyme is functionally identical to the lipase isolated from Pseudomonas Novo Sp. ATCC 21,808, and it is also identical or functionally identical to the enzyme employed by Applicant in work conducted during development of this invention.

The active site model provided by Laumen contains an ester-reacting serine hydroxyl portion, a hydrophobic pocket that binds a large lipophilic substituent, and a niche that will only accept a hydrogen atom such as shown in the drawing for phenyl acetate. In addition, Laumen's work has indicated that the enzyme requires for activity a small hydrophobic substituent attached to the chiral carbon in the substrate.

The active site model is applicable to acyclic as well as cyclic compounds.

Laumen et al, *J. Chem. Soc Chem. Commun.*, 1988. pages 598–600, discloses the preparation of certain secondary alcohols in high optical purity using the lipase from a Pseudomonas species. The lipase is the same or functionally the same enzyme employed in Applicant's invention.

Laumen et al, *J. Chem. Soc. Chem. Commun.*, 1988, pages 1459–1461, further discusses the preparation in high chemical and optical yield of certain secondary alcohols; the disclosed method uses the aforementioned ester hydrolase and vinyl acetate as an acyl donor.

Xie et al, *J. Chem. Soc. Chem Commun.*, 1988, pages 966-967, discloses the hydrolysis of six- and seven-membered ring acetates using the lipase from *Pseudomonas fluorescens*.

Wang et al, *Tetrahedron Letters* Vol. 30, (1989) pages 1917-1920 discloses a synthesis of cyanohydrins using an enzymatic esterification.

Manzocchi et al., *J. Chem. Soc. Perkin Trans. I.* 1987, (pp. 2753-57) and Deol et al, *Aust. J. Chem.*, 1976, (pp. 2459-67) illustrate the tedious preparation of chiral compounds using yeast fermentations.

Mukayama et al, *Chemistry Letters*, pp. 813-816, (1985) and Soai et al, *J. Chem. Soc. Chem. Commun.*, 1985, pages 138-139, illustrate chemical syntheses of chiral compounds.

SUMMARY OF THE INVENTION

In a highly preferred embodiment this invention relates to a process for the preparation of optically pure or substantially optically pure 1-phenyl-1,3-propanediols. Applicant's process can be used to prepare both optical isomers of this substance in high optical purity. Applicant's process does not use the type of resolution classically employed in organic chemistry. Instead, it uses a hydrolase based biocatalytic synthesis to introduce stereospecificity into a reaction sequence. In this manner, Applicant avoids the tedium and expense characteristic of classical resolution techniques, as well as the difficult isolations, low product concentrations, and mutation vagaries that are inherent in a fermentation process. Applicant's process can be extended to the preparation of other optically pure aryl alkylenediols.

Although not bound by any theory, it appears there are four significant characteristics of the active site of the Pseudomonas enzyme, which affect the reactivity and selectivity of the hydrolysis reaction used in this invention. These characteristics are:

(1) the reaction site—i.e., the site on the enzyme where the enzyme serine hydroxyl reacts with the ester carbonyl of the reactant, (2) the large lipophilic 'pocket' of the enzyme, (3) the small lipophilic binding site, and (4) the niche which will only accept a proton bonded to the chiral carbon of the reactant At present, not much is known about these four enzyme characteristics, or how they interact with one another. Consequently, in the case of novel substrates (such as those used by Applicant), there is insufficient basis to predict how substrate structural variations will effect enzymatic reactivity and/or selectivity. Therefore, Applicant's process is not predictable from the prior art.

To illustrate the invention, the preparation of optically pure S-1-phenyl-1,3-propanediol, by Applicant's reaction sequence is schematically set forth below:

REACTION SCHEME (A)

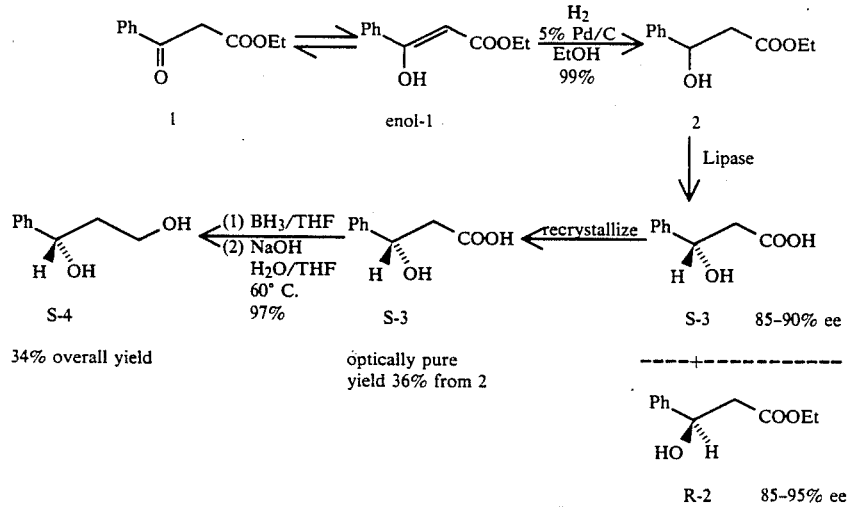

Ph = phenyl
Et = ethyl
THF = tetrahydrofuran

The yield percentages given above are illustrative and non limiting.

The products of Applicant's process, such as those illustrated by scheme (A), are useful as chemical intermediates. More particularly, they can be used to prepare materials with high optical specificity. Such preparations are highly useful, for example, in pharmaceutical synthesis where one optical form of a drug may be active and the other may not be. In such instances it is highly desirable to prepare the active optical isomer and to avoid or minimize formation of the inactive enantiomer. Such a stereospecific process can be conducted using a product of this invention.

For this invention, "substantially optically pure" signifies an optical purity equivalent of at least about an 85% enantiomeric excess (ee), and the term "optically pure" refers to an optical purity of 98% ee, or greater.

BRIEF DESCRIPTION OF THE DRAWING

The FIGURE is a depiction of the (prior art) active site steric model for the lipase from *Psuedomonas fluorescens*. The active site is the non shaded portion of the drawing. As shown, the active site model is an irregular, barrel shaped "pocket" of the enzyme which will accommodate a molecule such as phenyethyl acetate, the substance shown by formula in the drawing. Of particular interest is the portion of the enzymatic surface that will admit a small alkyl lipophilic portion, such as that to the right of the single bonded oxygen in phenyethyl acetate.

As indicated above, the FIGURE depicts the model as suggested by the art. As such, there was no understanding prior to this invention of the enzyme's active site being able to accept the presence of a lipophobic hydroxyl group, such as that which appears in Applicant's substrates. Stated another way, the art contemplated an enzyme surface which could accommodate a methyl or other lipophilic group (such as depicted in the drawing). Moreover, there was no understanding in the art that this site would also accept the sterically and ionically different hydroxyl group.

Therefore, until Applicant's invention, a skilled practitioner could have predicted that the lipophobic hydroxyl would prevent the enzyme from acting as a catalyst.

DESCRIPTION OF PREFERRED EMBODIMENTS

In one embodiment of this invention, Applicant provides a process for the separation of optical isomers of a compound having the formula:

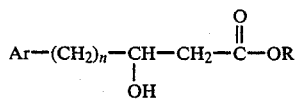
(I)

The process involves subjecting the racemate to be separated to the hydrolysis action of a lipase from *Pseudomonas fluorescens*. The enzyme preferentially hydrolyzes the S- form of the ester, thereby forming the acid. Due to the moderate selectivity of the reaction, the hydrolysis is preferably run to less than 50% conversion in order to afford the acid product in fairly high enantiomeric excess. The product of the hydrolysis is a mixture of the S-isomer of the acid:

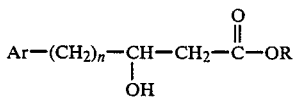
(II)

and the R-isomer of ester (I).

In this reaction, the nature of Ar and R, and the value of n is not critical, so long as the reaction takes place without poisoning the enzyme to an untoward extent, or violating the steric requirements of the enzyme. Thus, the aryl radical Ar may be a substituted or an unsubstituted aromatic, e.g., phenyl radical.

In a preferred embodiment, Ar is the phenyl radical, or a lightly substituted phenyl radical having up to about 10 carbon atoms. It is also preferred that the value of n be a small whole number. Preferably, n is equal to a small number ranging from zero to about six; most preferably, n is equal to zero.

The alcohol residue depicted by R can be selected from a wide variety of materials. In general, the nature of the radical R is not critical. Preferably, it is a lower alkyl radical having up to about four carbon atoms. Alcohols Providing such groups are readily available and inexpensive, and therefore well suited for this invention.

Alternatively, the R group has a substituent which enhances the rate of the hydrolysis. In this regard it is suggested that a chloro function in 2-chloroethanol or 2,2,2-trichloroethanol might be such an activating species; and therefore, 2-chloroethyl or 2,2,2-trichloroalkyl substituents might be R groups which are activating and highly useful in the process of this invention.

The hydrolysis reaction using the lipase is conducted in an aqueous medium having a pH in the range of from about 5.0 to about 9.0. Preferably, the process is conducted at a pH of about 7.0. The desired pH can be achieved and maintained with conventional buffers. It is also convenient to continuously add base by automatic titration, and thereby maintain the pH. The course of the reaction can be followed by monitoring the base added in this manner, and monitoring is a useful and preferred operational expedient.

The enzymatic hydrolysis is conducted at a mild temperature. A preferred temperature range is from about 5° C. to about 60° C. Preferably, the temperature is in the range of from about 15° C. to about 25.C. Temperatures outside these ranges can be used as long as the catalyst is not deactivated. Ambient temperatures are convenient and preferred.

The process of this invention is conveniently conducted at ambient pressures, and such pressures are preferred. Greater and lower pressures can be used, if desired.

The reaction time is not a truly independent variable, and is dependent to at least some extent on the activity of the enzyme, and on the reactivity of the substrate employed. The reaction temperature also has an effect on the reaction time. Generally speaking, the higher the temperature, the shorter the time. Typically, one employs a hydrolysis reaction time of from about 15 to about 30 hours. Times outside this range can be used, if desired.

A catalytic quantity of enzyme is employed. In general the amount of racemic substrate is from about 10 to about 100 times the weight of the enzyme used. An amount of racemate equal to from about 30 to about 70 times the weight of enzyme is preferred. The enzyme need not be in pure form; it may be used in an unpurified state, or immobilized or not immobilized. The aforementioned catalytic amounts are for unpurified enzymes. Lesser amounts of purified materials can be used The enzymatic hydrolysis may be conducted to less than complete conversion, if desired. As set forth more fully below, this process expedient can have some significant advantages. Thus, when an optically pure hydrolysis product is desired, it may be advantageous to conduct the hydrolysis to a completion rate of say 45–50 percent. On the other hand, when the unreacted substrate in optically pure form is the major objective, it may be desirable to conduct the hydrolysis to a somewhat higher conversion, say from about 55 to about 70 percent.

The hydrolysis process described above need not be conducted as a separate, isolated reaction. More specifically, it may be conducted in conjunction with other chemical reactions to provide a sequential, preparative technique for the production of specific optical isomers.

Such a sequence is an embodiment of this invention. For example, in the sequence of reactions depicted above in scheme (A), the acid product that is made by the enzymatic hydrolysis can be converted to a form that is soluble in water, such as a salt. After this transformation, the salt of the acid is readily separable by extraction from the unreacted ester, which is also present in the hydrolysis reaction mixture, by extraction of the ester from an aqueous solution of the acid. The extraction is conducted using a non polar solvent in which the salt is not readily soluble, and which is a comparatively good solvent for the ester that is present. Diethyl ether, di-n-butyl ether, ethyl acetate, and the like are suitable extraction solvents. One or more simple extractions or a continuous extraction may be used.

After removal of the ester portion of the hydrolysis reaction mixture, the acid can be regenerated from the salt by reacting a strong acid with the salt. Thereafter, the regenerated acid can, if desired, be purified to optical homogeneity by recrystallization using a suitable organic solvent such as an ether of the type illustrated above. For example, the acid may be recrystallized from tert-butyl methyl ether.

If desired, the purified optically pure acid can be used as a starting material to produce another compound in optically pure form. Thus, as illustrated by reaction sequence (A) above, and the examples which follow, the S-acid produced in the above described manner can be reduced with a suitable reducing agent (such as borane, diborane, and the like) to produce an aryl alkane diol which is optically pure. Likewise, recovered R ester obtained in the above described manner can be reduced (e.g., sodium borohydride) to afford the substantially optically pure diol antipode.

Conversion of the acid to its salt with a base, such as an alkali metal carbonate, bicarbonate, or similar strong base, can be conducted as apparent to one skilled in the art. Likewise, the process conditions used in the extraction discussed above, or in the regeneration of the acid from its salt, or in the recrystallization, or in the reduction of the purified acid, are non critical, and can be selected in general accordance with the art. Such reaction variables are illustrated by the examples which follow.

In the examples, certain materials are referred to by numerals. The numerals employed are those used in Reaction Sequence (A) above.

EXAMPLE 1

Catalytic Hydrogenation of Ethyl Benzoylacetate

Ethyl benzoylacetate (1) (19.21 g; 0.10 mol) was dissolved in 95% ethanol (100 mL) in a pressure bottle. The bottle was purged with nitrogen and 5% palladium on carbon (960 mg; 5 weight %) was added. The vessel was placed under 45 psi $H_2$ and shaken on a Parr apparatus for 14 hours, at which time $H_2$ uptake had halted and thin layer chromatographic analysis indicated (1) was present. The reaction mixture was suction-filtered through Celite with a top sand layer (to prevent channels) and eluted with ether to remove the catalyst. The filtrate was concentrated to afford (2), racemic ethyl 3-phenyl-3-hydroxypropionate (19.17 g; 99%) which was pure by tlc and $^1$H nmr analysis. $^1$H nmr (300 MHz, CDCl$_3$): 7.4–7.2 (5H, m); 5.130(1H,dd,J=4.36, 8.48 Hz); 4.178 (2H, q, J=7.17 Hz); 3.2(1H, br s); 2 764(1H, dd, J=8.58, 16.30 Hz); 2.691 (1H, dd, J=4.33, 16.33 Hz); 1.259(3H, t, J=7.17 Hz). IR (neat film, cm$^{-1}$) 3450 (s,b); 1720(s); 1605(w). EIMS (m/e): 194 (M$^+$); 165 (2%, M$^+$- Et); 149 (5%, M$^+$-EtO).

It was found that 10% palladium on charcoal gave a faster reaction than reported above.

As indicated, the reaction conditions employed in the preceding example gave a near quantitative yield of racemic ester, and required no purification of the product. Hence, the use of hydrogenation with palladium on charcoal catalyst to reduce a β-ketoester constitutes a highly preferred method for preparing a racemic ester that is intended for use as a raw material in the process of this invention. Consequently, preferred embodiments of this invention comprise use of this synthesis technique, in conjunction with the biocatalytic process described above and illustrated below.

EXAMPLE 2

Enxymatic Hydrolysis of Ester

Racemic ester (2) (17.78 g; 91.54 mmol) was combined with pH 7 phosphate buffer (35 mL) in a 250 mL beaker. This mixture was placed on an automatic titrator and the pH was adjusted to 7.00. Lipase P-30 (350 mg; a lipase of *Pseudomonas fluorescens* obtained from Amano International Enzyme Co.) was added and the hydrolysis commenced. The reaction mixture was maintained at pH 7.00 by automatic titration and followed by the uptake of 1.000 N NaOH. After 20 hours at room temperature, 41.45 mL of 1.000 N NaOH had been consumed (45.3% conversion) and the reaction was halted. The reaction mixture was diluted with water (20 mL) and saturated NaHCO$_3$(20 mL), then extracted with ether (3×40 mL). The combined organic solution was extracted with saturated NaHCO$_3$ (10 mL), dried (MgSO$_4$), and concentrated to afford 8.22 g (46%) of R-(2), i.e., the R-form of ethyl 3-phenyl-3-hydroxypropionate, $[\alpha]_D^{22}+42.3°$ (c. 1.228, chloroform). The R configuration was indicated by comparison with the literature value for the S-antipode ($[\alpha]_D^{22}-40.8°$ (c. 1.03, chloroform), Soai et al *J. Chem. Soc. Chem. Comm.* 1985. 138).

The combined aqueous solution was acidified to pH 1 with 3 N HCl (35 mL) and extracted with ether (4×40 mL). The extracts were dried (MgSO$_4$) and concentrated to afford 6.74 g (44%) of S-(3), i.e. S-3-phenyl-3-hydroxypropionic acid. This material was recrystallized from warm t-butyl methyl ether (50 mL) by the addition of hexanes (50 mL) and cooling to room temperature. Further cooling to −20° C. gave no apparent increase in crystal mass. Optically Pure S-3-phenyl-3-hydroxypropionic acid, (>98% ee as indicated by $^1$H nmr analysis of the MTPA derivative of the corresponding methyl ester) (5.45 g, 36%) was collected as white needles, mp 118°–119° C. $^1$H nmr (300 MHz, CD$_3$CN): 7.6–7.2 (5H, m); 5.07 (1H, t, J=6.65 Hz); 4.9 (2H, br s); 2.68 (2H, d, J=6.73 Hz). IR (KBr, cm$^{-1}$): 3500–2400 (s,b); 1700 (s); 1595(w); 1505(w). EIMS (m/e): 166 (M$^+$); 148 (2%, M$^+$−H$_2$O). $[\alpha]_D^{20}-22.7°$ (c/ 1.034, CH$_3$OH).

Anal.: Calc. for C$_9$H$_{10}$O$_3$: C, 65.05; H, 6.07; Found: C, 65.28; H, 6.00.

EXAMPLE 3

Borane Reduction to S-1-Phenyl-1,3-Propanediol

Optically pure hydroxy-acid S-(3) (1.66 g; 10.0 mmol) was dissolved in tetrahydrofuran (THF) (20 mL) and cooled to 0° C. A 1.0 M solution of borane in THF (21 mL; 21 mmol; 2.1 equiv) was added (frothing) and the reaction mixture was warmed to room temperature for one hour. Aqueous sodium hydroxide (10%, 20 mL) was added and the mixture was heated to 60° C. for 3 hours to cleave the borate complex. The mixture was cooled to room temperature and extracted with ether (3×35 mL). The combined extracts were dried (MgSO$_4$) and concentrated to afford 1.59 g of crude diol which solidified upon chilling (−20° C.). This was dissolved in methylene chloride (7.5 mL, 5 mL/g) and hexanes (7.5 mL, one volume) was added. This resulted in a phase separation which upon cooling (−20° C.) overnight afforded optically pure S-1-phenyl-1,3-propanediol (S-(4)) as white needles, mp 63°-65° C. H nm (300 MHz, CDCl$_3$): 7.4–7.2 (5H, n); 4.869 (1H, dd, J=4.04, 8.52 Hz); 3.789 (2H, m); 3.6 (1H, br s); 3.14 (1H, Br s); 2.05–1.8 (2H, m). IR (KBr, cm$^{-1}$): 3350 (s,b); 1605 (w); 1485 (w). EIMS (m/e); 152 (M+); 134 (M+ −H$_2$O); 107 (M+ −CH$_2$CH$_2$OH).

Anal.: Calc. for C$_9$H$_{12}$O$_2$; C; 71.03; H, 7.95; Found: C, 70.91; H, 7.77. $[\alpha]_D^{20}$ −39.9 (c. 0.862, CH$_3$OH$_3$).

Example 2 illustrates a process for the separation of optical isomers in a racemic carboxylic ester having formula (I). The process comprises hydrolyzing the racemate in the presence of lipase from *Pseudomonas fluorescens*. The product mixture comprises an acid of formula (II) and an ester of formula (I).

Example 2 also illustrates a process which comprises the hydrolysis, followed by conversion of the acid produced to a salt, e.g., an alkali metal salt. In the process of the Example, NaHCO$_3$ was used as the base. Other bases capable of reacting with the acid can be used. Such other bases are known to a skilled practitioner. In general they are metal-containing bases having sufficient basicity to completely or substantially completely convert the acid to a salt. If desired, organic bases can be used.

Example 2 also illustrates the separation of acid produced on hydrolysis from the unreacted ester. The separation comprises extraction of the ester with an organic solvent such as an ether.

In summary, Examples 2 and 3 illustrate a process for the preparation of S-1-phenyl-1,3-propanediol of high optical purity. The process comprises (a) hydrolyzing racemic ethyl 3-phenyl-3-hydroxypropionate in the presence of lipase from *Pseudomonas fluorescens* such that the hydrolysis is conducted to a conversion of from about 45 to about 50%, (b) converting the S-acid thereby produced to a water soluble salt thereof, (c) separating the salt from the unreacted R-ester by extraction of the unreacted ester with an organic solvent, (d) acidifying the salt to recover the S-acid, (e) purifying the recovered acid to enhance the optical purity, and (e) reducing the purified acid thereby produced to form the diol in high optical purity.

The process of this invention also comprises a process for the preparation of R-1-phenyl-1,3-propanediol of high optical purity, said process comprising (a) hydrolyzing racemic 3-phenyl-3-hydroxypropionate in the presence of lipase from *Pseudomonas fluorescens* such that the hydrolysis is conducted to a conversion within the range of from about 55 to about 70 percent, (b) converting the S-acid thereby produced to a soluble salt thereof, and separating said salt and the unreacted R-ester by extracting said R-ester into an organic solvent, and (d) reducing said unreacted ester to form said R-1-phenyl-1,3-propanediol of high optical purity. Alternatively, the R-ester obtained in Example 2 above (enzymatic hydrolysis <50% conversion) can afford R-1-phenyl-1,3-propanediol of high optical purity, said process comprising (a) chemical hydrolysis of the unreacted recovered R-ethyl 3-phenyl-3-hydroxypropionate, (b) followed by purification of the resulting R-3-phenyl-3-hydroxypropionic acid to obtain a high optical purity product and (c) reducing the acid to form the R-1-phenyl-1,3-propanediol. This is illustrated by the following examples.

EXAMPLE 4

Preparation of R-3-Phenyl-3-hydroxypropionic Acid

Ethyl R-3-phenyl3-hydroxypropionate recovered from enzymatic hydrolysis (1.00 g; 5.15 mmol), 90% ee, was dissolved in methanol (10 mL). A 10% aqueous solution of sodium hydroxide (10 mL; excess) was added and the reaction mixture was stirred at room temperature overnight, at which time no ester was visible by tlc analysis. The reaction mixture was diluted with ether (30 mL) and extracted with saturated sodium bicarbonate (3×10 mL). The ethereal solution was discarded and the combined aqueous extracts were acidified to pH 1 with 3 N HCl and extracted with ether (4×30 mL). The latter combined extracts were dried (MgSO$_4$) and concentrated to afford 756 mg (88%) of R-acid (3). This was recrystallized from warm t-butyl methyl ether (7.5 mL; 10 mL/g) by the addition of one volume of hexanes and chilling to afford 587 mg (69%) of optically pure R-3, mp 114–116 C (>98% ee as indicated by $^1$H nmr analysis of the MTPA derivative of the corresponding methyl ester).

All achiral properties of (3) are as reported above. $[\alpha]_D^{20}$ +22.8° (c. 1.22, methanol).

EXAMPLE 5

Preparation of R-3-Phenyl-1,3-propanediol

Hydroxy-acid R-(3) (>98% ee; 166 mg; 1.00 mmol) was dissolved in THF (2 mL) and cooled to 0° C. A 1.0 M solution of borane in THF (2.1 mL; 2.1 mmol; 2.1 equiv.) was added and the reaction mixture was warmed to room temperature. After one hour at room temperature no (3) remained by tlc analysis, and a 10% aqueous solution of sodium hydroxide (2 mL., excess) was added. The resulting mixture was heated to 60° C. for three hours, cooled to room temperature, diluted with water (10 mL), and extracted with ether (3×20 mL). The combined extracts were dried (MgSO$_4$) and concentrated to afford 146 mg (96%) of R-(4), 3-phenyl-1,3-propanediol.

All achiral properties of (4) are as reported above. $[\alpha]_D^{20}$ +37.6° (c. 0.830, CH$_3$OH).

The process of this invention can be extended to the preparation of other R- or S-aryl alkylidene diols by conducting the process illustrated by the above Examples with other racemic esters having formula (I).

The invention has been described above with particular reference to preferred embodiments. A skilled practitioner familiar with the above detailed description can make many modifications and substitutions without departing from the scope and spirit of the appended claims.

I claim:

1. A process for the separation of the optical isomers in a racemic carboxylic acid ester having the formula:

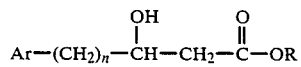

wherein Ar is a phenyl or substituted phenyl radical, n is equal to a small whole number within the range of 0 to about 4, and R is a lower alkyl or substituted alkyl radical;

said process comprising hydrolyzing said racemate in the presence of lipase from *Pseudomonas fluorescens* to obtain a mixture of the S-isomer of the acid,

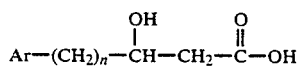

and the unreacted R-isomer of said ester.

2. The process according to claim 1 wherein Ar is phenyl, and n is equal to zero.

3. The process according to claim 1 wherein the hydrolysis is followed by conversion of said acid to an alkali metal salt, and the separation of said salt from said R-ester by extraction of said ester into an organic solvent.

4. The process according to claim 2 wherein the hydrolysis is followed by conversion of said acid into an alkali metal salt by treatment of the hydrolysis reaction mixture with a base, followed by separation of said R-ester from said salt by extraction of said R-ester with an organic solvent.

5. The process of claim 2 wherein the hydrolysis is conducted to a conversion of 45–50 percent to afford said acid in enantiomeric excess of 85–90 percent.

6. Process for the preparation of pure S-1-phenyl-1,3-propanediol of high optical purity, said process comprising (a) hydrolyzing racemic ethyl 3-phenyl-3-hydroxypropionate in the presence of lipase from *Pseudomonas fluorescens* such that the hydrolysis is conducted to a conversion of from about 45 to about 50%, (b) converting the S-acid thereby produced to a water soluble salt thereof, (c) separating said salt from the unreacted R-ester by extraction of said unreacted ester with an organic solvent, (d) acidifying said salt to recover said S-acid, (e) purifying said recovered acid to optical purity, and (e) reducing the purified acid thereby produced to form said diol of high optical purity.

7. Process for the preparation of pure R-1-phenyl-1,3-propanediol, said process comprising (a) hydrolyzing racemic ethyl 3-phenyl-3-hydroxypropionate in the presence of a lipase from *Pseudomonas* fluorescens such that the hydrolysis is conducted to a conversion within the range of from about 45 to about 50 percent, (b) converting the S-acid thereby produced to a water soluble salt thereof, separating said salt and the unreacted R-ester by extracting said R-ester into an organic solvent, (d) chemically hydrolyzing said R-ester to the corresponding S-acid, (e) purifying said R-acid to enhance its optical purity, and (f) reducing the purified acid thereby produced to form said pure diol of high optical purity.

* * * * *